(12) United States Patent
Zeng

(10) Patent No.: US 8,433,038 B2
(45) Date of Patent: Apr. 30, 2013

(54) ACTUAL SKIN INPUT DOSE RATE COMPUTING DEVICE AND METHOD AND X-RAY MACHINE

(75) Inventor: Xueming Zeng, Beijing (CN)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 386 days.

(21) Appl. No.: 12/823,014

(22) Filed: Jun. 24, 2010

(65) Prior Publication Data
US 2010/0329430 A1  Dec. 30, 2010

(30) Foreign Application Priority Data
Jun. 26, 2009 (CN) .......................... 2009 1 0146285

(51) Int. Cl.
*H05G 1/42* (2006.01)

(52) U.S. Cl.
USPC ............................................ 378/97; 378/205

(58) Field of Classification Search .................... 378/97, 378/205, 207, 210
See application file for complete search history.

(56) References Cited

U.S. PATENT DOCUMENTS

| | | |
|---|---|---|
| 5,694,449 A | 12/1997 | Aragones |
| 5,798,528 A | 8/1998 | Butsch et al. |
| 6,330,299 B1 | 12/2001 | Curtis et al. |
| 6,422,751 B1 | 7/2002 | Aufrichtig et al. |
| 6,934,362 B2 | 8/2005 | Scheuering |
| 2002/0136356 A1* | 9/2002 | Vallin et al. .................. 378/205 |
| 2005/0002489 A1* | 1/2005 | Scheuering .................... 378/97 |
| 2005/0152498 A1 | 7/2005 | Mungilwar |

\* cited by examiner

*Primary Examiner* — Hoon Song
(74) *Attorney, Agent, or Firm* — Armstrong Teasdale LLP (57) ABSTRACT

An actual skin input dose rate computing device includes a distance sensor disposed in a direction directly opposite to said subject and close to the center of an X-ray beam but not within said X-ray beam and an angle sensor disposed at said X-ray source as well as a computing unit.

17 Claims, 3 Drawing Sheets

ACTUAL SKIN INPUT DOSE RATE COMPUTING DEVICE AND METHOD AND X-RAY MACHINE

CROSS REFERENCE TO RELATED APPLICATIONS

This application claims the benefit of Chinese Patent Application No. 200910146285.9 filed Jun. 26, 2009, which is hereby incorporated by reference in its entirety.

BACKGROUND OF THE INVENTION

The present invention generally relates to the field of medical X-ray machines and more particularly relates to an actual skin input dose rate computing device and method and an X-ray machine.

At present, X-ray machines have been increasingly used in medical field. An X-ray machine images a subject by emitting X-ray through the subject. The doctor diagnoses and treats the subject based on the resulting image. However, as is well known, X-ray is harmful to the human body. Therefore, the X-ray dose rate incident on the subject skin needs to be known, such that the exposure time can be effectively controlled in order to minimize the harm caused to the subject by X-ray.

In Germany and some other countries in Europe, X-ray machines used in hospitals, e.g. C-arm X-ray machines, are required to provide DAP (Dose Area Product) to indicate the dose applied to the subject.

In the United States, the latest 21CFR (Title 21 of the Code of Federal Regulations) 1020.32(K) requires that the values of AKR (Air Kerma Rate) and CAR (Cumulative Air Kerma) at a given reference position should be displayed. For fluoroscopic devices produced on and after Jun. 10, 2006, AKR and CAR should be displayed at the operating position of the user.

In 21CFR 1020.32 (K), it is pointed out that for an X-ray system, the reference position is fixed, i.e. the position 30 cm above the upper surface of an X-ray detector.

According to the above requirement, a doctor could know a total absorbed dose or dose rate at a given reference position. However, the doctor usually cannot place the subject right at the reference position, but instead places the subject at the best diagnostic position. Thus, the doctor cannot know the actual skin input dose. The actual skin input dose is different from the input dose at the reference position. Sometimes actual skin input dose rate might be three times higher than the input dose rate at the reference position or even more. Therefore, even if the skin dose rate at the reference position is very low, it could still hurt the skin of the subject, because the actual skin input dose rate might be three times higher than the skin dose rate at the reference position or more, or even up to tens of times higher.

U.S. Pat. No. 6,330,299 discloses a system and method for determining the dose area product in an X-ray imaging system, which computes DAP based on a set of X-ray specification and image specification and then obtains the skin input dose rate RR at the reference position (as defined in 21CFR 1020.32 (K)).

U.S. Pat. No. 6,934,362 discloses an X-ray system and method for determining an effective skin input dose in an X-ray examination. In this patent, the skin input dose is obtained by dividing the measured DAP by exposed skin input area, which is calculated from the exposed area in the film or image intensifier plane.

U.S. Patent Publication No. 2005/0152498 discloses a method for computing the ray dose rate at a given position, which creates a table during the machine design and looks up the ray dose rate in the table based on the kilovolt and current values of the exposure parameters.

The technical solutions in the disclosed patents and patent applications mentioned above can only give the input dose rate at a specified reference position, but none of them can give the actual skin input dose rate.

There is a method for measuring the actual skin input dose rate at present, which measures the skin input dose rate in real time by placing a dose rate testing instrument on the skin surface of the subject. However, due to the placement of the dose rate testing instrument on the skin surface, the dose rate testing instrument will appear in the X-ray images, thereby impeding the doctor diagnosing diseases. This is highly infeasible in a practical surgery.

BRIEF DESCRIPTION OF THE INVENTION

The main problem the present invention solves is to provide an effective and feasible actual skin input dose rate computing device and method and an X-ray machine.

In order to solve the above problem, a technical solution of the actual skin input dose rate computing device of the present invention is described herein.

In one aspect, the actual skin input dose rate computing device is used in an X-ray machine, said X-ray machine comprising an X-ray source, an X-ray detector disposed opposite to said X-ray source and a supporting means for supporting a subject.

The device includes a distance sensor disposed in a direction directly opposite to said subject and close to the center of an X-ray beam but not within said X-ray beam, and an angle sensor disposed at said X-ray source as well as a computing unit. The computing unit includes a judgment unit for deciding whether the angle Φ sensed by the angle sensor is greater than or equal to 90 degrees or is less than 90 degrees, and a result unit for obtaining the actual skin input dose rate according to the result of the judgment unit and the relationship between the skin input dose rate at a reference position and the actual skin input dose rate.

Further, said result unit comprises a first unit and a second unit, wherein if the angle Φ sensed by said angle sensor is greater than or equal to 90 degrees, said first unit computes the actual skin input dose rate using the following equation:

$$R_S = \frac{D_1^2}{(D_2 + D_3)^2} \times R_R$$

wherein $D_1$ is a constant and indicates the distance between said X-ray source and the reference position, $D_2$ is a constant and indicates the distance between said X-ray source and said distance sensor, $D_3$ is the distance sensed by said distance sensor and $R_R$ is the skin input dose rate at the reference position;

If the angle Φ sensed by said angle sensor is less than 90 degrees, said second unit computes the actual skin input dose rate using the following equation:

$$R_S = \frac{D_1^2}{\left(D_2 + D_3 + \frac{D_5}{\cos\Phi}\right)^2} \times R_R \times e^{-K \frac{D_5}{\cos\Phi}(0 \oplus D_{AL})}$$

wherein $D_1$ is a constant and indicates the distance between said X-ray source and the reference position, $D_2$ is a constant and indicates the distance between said X-ray source and said distance sensor, $D_3$ is the distance sensed by said distance sensor, $R_R$ is the skin input dose rate at the reference position, $D_5$ is the thickness of said supporting means, K is the dose absorbing factor of AL, and $D_{AL}$ is the equivalent aluminum attenuation value of said supporting means.

In another aspect, a technical solution is embodied as an actual skin input dose rate computing method that is performed by an X-ray machine having an X-ray source, an X-ray detector disposed opposite to the X-ray source, and a supporting means for supporting a subject. The computing method includes an distance sensing step including sensing a distance $D_3$ by a distance sensor disposed in a direction directly opposite to the subject and close to the center of an X-ray beam but not within the X-ray beam.

The method also includes an angle sensing step including sensing an angle $\Phi$ by an angle sensor disposed at said X-ray source.

The method also includes a decision step including deciding whether the angle $\Phi$ sensed by said angle sensor is greater than or equal to 90 degrees or is less than 90 degrees.

The method also includes a computing step including obtaining said actual skin input dose rate according to the result of said decision step and the relationship between the skin input dose rate at a reference position and the actual skin input dose rate.

If the result of said decision step is that the angle $\Phi$ is greater than or equal to 90 degrees, the actual skin input dose rate is computed using the following equation:

$$R_S = \frac{D_1^2}{(D_2 + D_3)^2} \times R_R$$

wherein $D_1$ is a constant and indicates the distance between said X-ray source and the reference position, $D_2$ is a constant and indicates the distance between said X-ray source and said distance sensor, $D_3$ is the distance sensed by said distance sensor and $R_R$ is the skin input dose rate at the reference position;

If the result of said decision step is that the angle $\Phi$ is less than 90 degrees, the actual skin input dose rate is computed using the following equation:

$$R_S = \frac{D_1^2}{\left(D_2 + D_3 + \frac{D_5}{\cos\Phi}\right)^2} \times R_R \times e^{-K\frac{D_5}{\cos\Phi}(0 \oplus D_{AL})}$$

wherein $D_1$ is a constant and indicates the distance between said X-ray source and the reference position, $D_2$ is a constant and indicates the distance between said X-ray source and said distance sensor, $D_3$ is the distance sensed by said distance sensor, $R_R$ is the skin input dose rate at the reference position, $D_5$ is the thickness of said supporting means, K is the dose absorbing factor of AL, and $D_{AL}$ is the equivalent aluminum attenuation value of said supporting means.

In another aspect of the present invention, there is provided an X-ray machine, the technical solution of said X-ray machine including an X-ray source, an X-ray detector disposed opposite to the X-ray source, a supporting means for supporting a subject, and an actual skin input dose rate computing device, wherein the actual skin input dose rate computing device includes a distance sensor disposed in a direction directly opposite to the subject and close to the center of an X-ray beam but not within the X-ray beam, an angle sensor disposed at the X-ray source, and a computing unit. The computing unit includes a judgment unit for deciding whether the angle $\Phi$ sensed by the angle sensor is greater than or equal to 90 degrees or is less than 90 degrees, and a result unit for obtaining an actual skin input dose rate according to the result of the judgment unit and the relationship between the skin input dose rate at a reference position and the actual skin input dose rate.

Further, said result unit comprises a first unit and a second unit, wherein if the angle $\Phi$ sensed by said angle sensor is greater than or equal to 90 degrees, said first unit computes the actual skin input dose rate using the following equation:

$$R_S = \frac{D_1^2}{(D_2 + D_3)^2} \times R_R$$

wherein $D_1$ is a constant and indicates the distance between said X-ray source and the reference position, $D_2$ is a constant and indicates the distance between said X-ray source and said distance sensor, $D_3$ is the distance sensed by said distance sensor and $R_R$ is the skin input dose rate at the reference position;

If the angle $\Phi$ sensed by said angle sensor is less than 90 degrees, said second unit computes the actual skin input dose rate using the following equation:

$$R_S = \frac{D_1^2}{\left(D_2 + D_3 + \frac{D_5}{\cos\Phi}\right)^2} \times R_R \times e^{-K\frac{D_5}{\cos\Phi}(0 \oplus D_{AL})}$$

wherein $D_1$ is a constant and indicates the distance between said X-ray source and the reference position, $D_2$ is a constant and indicates the distance between said X-ray source and said distance sensor, $D_3$ is the distance sensed by said distance sensor, $R_R$ is the skin input dose rate at the reference position, $D_5$ is the thickness of said supporting means, K is the dose absorbing factor of AL, and $D_{AL}$ is the equivalent aluminum attenuation value of said supporting means.

Compared to the prior art, advantageous effects achieved by the actual skin input dose rate computing device and method and X-ray machine of the present invention are described herein.

The present invention employs a distance sensor and an angle sensor to sense the distance to a subject and the angle between a plumb line and the central line of an X-ray beam, and computes the actual skin input dose rate according to the relationship between said angle and distance and the skin input dose rate at a reference position, thereby being able to precisely obtain an actual skin input dose rate, which is very practical and effective such that the doctor could know the actual skin input dose rate upon the subject so that the subject could be protected effectively and the harm caused to the subject by X-ray could be minimized while an effective and correct diagnosis for the subject could be made.

BRIEF DESCRIPTION OF THE DRAWINGS

The present invention will be more thoroughly understood by the skilled in the art from the following description in combination with the drawings, in which like reference number refers to like elements.

DETAILED DESCRIPTION OF THE INVENTION

In the following the features and advantages of the present invention are described by means of exemplary embodiments.

Figure 1:
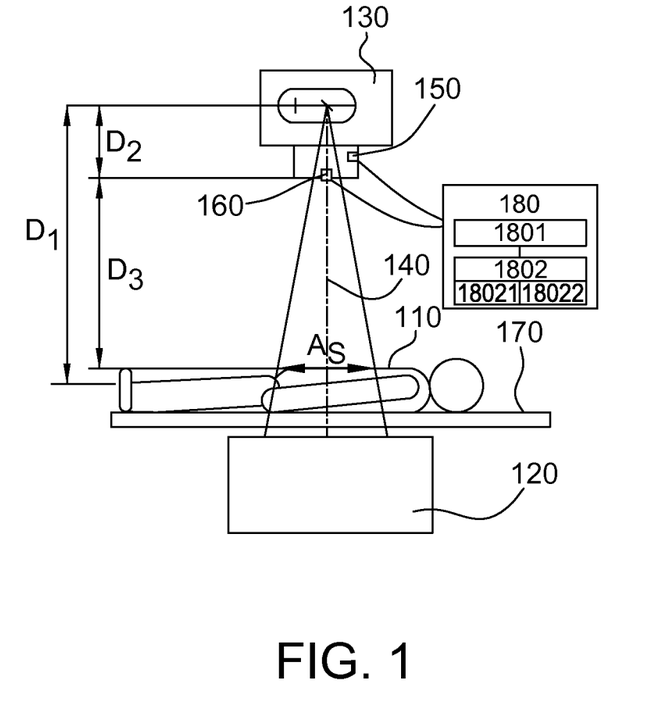
FIG. 1 is the diagram of the actual skin input dose rate computing device in an X-ray machine according to the present invention.

As shown in FIG. 1, it is illustrated an actual skin input dose rate computing device in an X-ray machine. In this figure, the illustrated X-ray machine comprises an X-ray source 130, an X-ray detector 120 (could also be an image intensifier) disposed opposite to said X-ray source 130 and a supporting means 170 for supporting a subject 110. It can be seen from FIG. 1 that said device comprises a distance sensor 160 disposed in a direction directly opposite to said subject and close to the center 140 of an X-ray beam but not within said X-ray beam, and an angle sensor 150 disposed at said X-ray source 130, as well as a computing unit 180; wherein said computing unit 180 comprises: 180.

The computing unit 180 includes a judgment unit 1801, for deciding whether the angle Φ sensed by said angle sensor 150 is greater than or equal to 90 degrees or is less than 90 degrees, and a result unit 1802 for obtaining the actual skin input dose rate according to the result of the judgment unit 1801 and the relationship between the skin input dose rate at a reference position and the actual skin input dose rate.

As to said result unit 1802, it may comprise a first unit 18021 and a second unit 18022, wherein if the angle Φ sensed by said angle sensor 150 is greater than or equal to 90 degrees, said first unit 18021 computes the actual skin input dose rate using Equation (1):

$$R_S = \frac{D_1^2}{(D_2 + D_3)^2} \times R_R \qquad \text{Eq. (1)}$$

wherein $D_1$ is a constant and indicates the distance between said X-ray source 130 and the reference position, $D_2$ is a constant and indicates the distance between said X-ray source 130 and said distance sensor 160, $D_3$ is the distance sensed by said distance sensor 160 and $R_R$ is the skin input dose rate at the reference position, If the angle Φ sensed by said angle sensor 150 is less than 90 degrees, said second unit 18022 computes the actual skin input dose rate using Equation (2):

$$R_S = \frac{D_1^2}{\left(D_2 + D_3 + \frac{D_5}{\cos\Phi}\right)^2} \times R_R \times e^{-K\frac{D_5}{\cos\Phi}(0 \oplus D_{AL})} \qquad \text{Eq. (2)}$$

wherein $D_1$ is a constant and indicates the distance between said X-ray source and the reference position, $D_2$ is a constant and indicates the distance between said X-ray source 130 and said distance sensor 160, $D_3$ is the distance sensed by said distance sensor 160, $R_R$ is the skin input dose rate at the reference position, $D_5$ is the thickness of said supporting means, K is the dose absorbing factor of AL, and $D_{AL}$ is the equivalent aluminum attenuation value of said supporting means 170.

From the above it can be seen that, for the relationship between the X-ray source 130 and the subject 110, there can only be two types: one type is the X-ray source 130 being above the subject 110, as in FIG. 3, i.e. Φ is greater than or equal to 90 degrees, where the actual skin input dose rate can be computed based on the distance measured by the distance sensor 160 and some constants; the other type is the X-ray source 130 being below the subject 110 (or the supporting means 170), i.e. Φ is less than 90 degrees, where the dose attenuation due to the thickness of the supporting means 170 and the angle Φ must be considered in order to compute the actual skin input dose rate. For the situation of Φ being less than 90 degrees, there is a special case, i.e. Φ is equal to 0 degree. In this case only the dose attenuation due to the thickness of the supporting means 170 needs to be considered and the dose attenuation due to the angle needs not to be considered.

Figure 3:
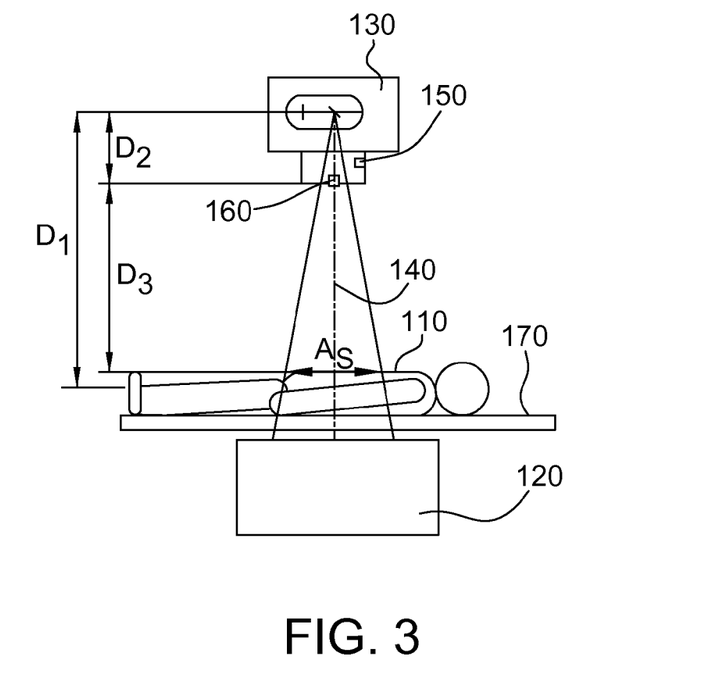
FIG. 3 is the diagram of an embodiment of the angle Φ sensed by an angle sensor being greater than or equal to 90 degrees.

As shown in FIG. 3, it is illustrated the diagram of an embodiment of the angle Φ sensed by the angle sensor being greater than or equal to 90 degrees.

As is well known, the ratio of the X-ray beam area at the reference position to the actual X-ray beam area at the subject skin is shown in Equation (3):

$$\frac{A_R}{A_S} = \frac{D_1^2}{(D_2 + D_3)^2} \qquad \text{Eq. (3)}$$

wherein $A_R$ is the X-ray beam area at the reference position; and $A_S$ is the actual X-ray beam area at the subject skin.

It is also known that the DAP rate at the reference position $DAP_R$ is equal to the actual DAP rate at the subject skin $DAP_S$, as shown in Equation (4):

$$DAP_R = DAP_S \qquad \text{Eq. (4)}$$

$DAP_R$ and $DAP_S$ are computed respectively as follows:

$$DAP_R = R_R \times A_R \qquad \text{Eq. (5)}$$

$$DAP_S = R_S \times A_S \qquad \text{Eq. (6)}$$

wherein $R_R$ is the skin input dose rate at the reference position and $R_S$ is the actual skin input dose rate.

We substitute equation (5) and (6) respectively into equation (4), and get:

$$R_S = \frac{A_R}{A_S} \times R_R \qquad \text{Eq. (7)}$$

Then we substitute equation (3) into the above equation and get:

$$R_S = \frac{D_1^2}{(D_2 + D_3)^2} \times R_R \qquad \text{Eq. (1)}$$

wherein $D_1$ is a constant and indicates the distance between said X-ray source 130 and the reference position, $D_2$ is a constant and indicates the distance between said X-ray source 130 and said distance sensor 160, $D_3$ is the distance sensed by said distance sensor 160 and $R_R$ is the skin input dose rate at the reference position (which can be computed according to U.S. Pat. No. 6,330,299).

Therefore, the actual skin input dose rate in the case of Φ being greater than or equal to 90 degrees can be computed by equation (1).

Figure 4:
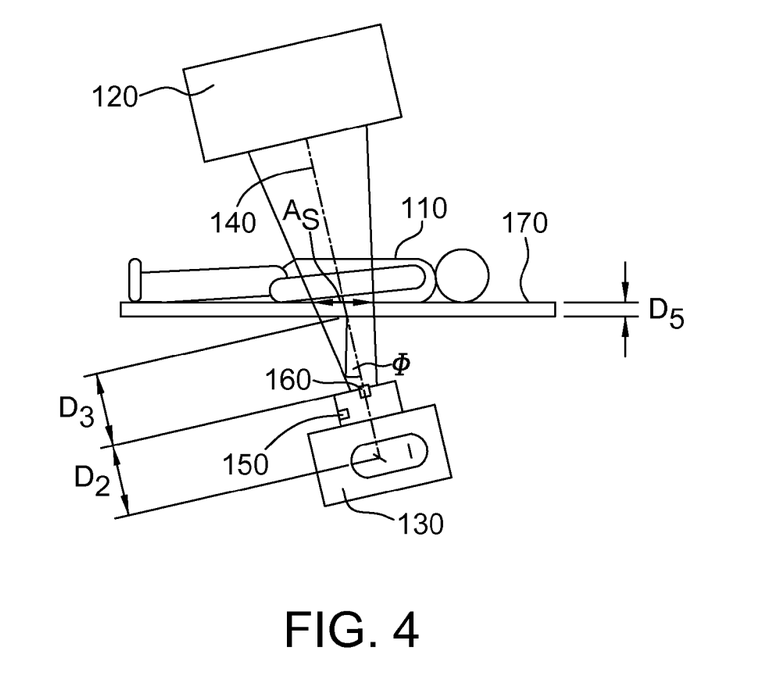
FIG. 4 is the diagram of an embodiment of the angle Φ sensed by an angle sensor being less than 90 degrees.

For the case where Φ is less than 90 degrees, as shown in FIG. 4, the X-ray source 130 is located below the subject 110 (or supporting means 170), so the X-ray emitted by the X-ray source 130 can reach the subject 110 only after passing through the supporting means 170. Therefore, assume the equivalent aluminum AL attenuation value of the supporting means 170 is $D_{AL}$, because the dose attenuation factor of aluminum under the given KV (kilovolts) is K, so after taking the dose attenuation element into consideration, equation (1) becomes:

$$R_S = \frac{D_1^2}{\left(D_2 + D_3 + \frac{D_5}{\cos\Phi}\right)^2} \times R_R \times e^{-K\frac{D_5}{\cos\Phi}(0 \oplus D_{AL})} \quad \text{Eq. (2)}$$

For the case $D_{AL}=0$, equation (2) should become:

$$R_S = \frac{A_R}{A_S} \times R_R = \frac{D_1^2}{\left(D_2 + D_3 + \frac{D_5}{\cos\Phi}\right)^2} \times R_R$$

For the case $D_{AL} \neq 0$, equation (2) becomes:

$$R_S = \frac{D_1^2}{\left(D_2 + D_3 + \frac{D5}{\cos\Phi}\right)^2} \times R_R \times e^{-K\frac{D5}{\cos\Phi}}$$

For an X-ray machine, $D_1$, $D_2$ and $D_5$ are constants, and in this example are assumed to be 70 cm, 18 cm and 3 cm respectively. In this example the equivalent aluminum attenuation of the supporting means 170 is $D_{AL}=0.7$ mm and the exposure condition is 70 k, then K=0.072, and according to U.S. Pat. No. 6,330,299 we can compute:

$$R_R=1 \; \mu Gy/min \quad \text{Eq. (8)}$$

As in the case shown in FIG. 3, the distance $D_3$ sensed by the distance sensor 160 is 30 cm and the angle Φ sensed by the angle sensor 150 is 180 degrees.

The judgment unit 1801 decides that this angle Φ (180 degrees) is greater than 90 degrees and the result unit 1802 obtains said actual skin input dose rate according to the result of said judgment unit 1801 and the relationship between the skin input dose rate at a reference position and the actual skin input dose rate.

Wherein, since the decision made by the judgment unit 1801 is that the angle Φ is greater than 90 degrees, the fist unit 18021 is then initiated, that is, computing the actual skin input dose rate with Equation (1):

$$R_S = \frac{D_1^2}{(D_2+D_3)^2} \times R_R$$

$$R_S = \frac{70^2}{(18+30)^2} \times 1 = 2.13(\mu Gy/min)$$

As in the case shown in FIG. 4, the distance $D_3$ sensed by the distance sensor 160 is 30 cm and the angle Φ sensed by the angle sensor 150 is 30 degrees.

The judgment unit 1801 decides that this angle Φ (30 degrees) is less than 90 degrees and the result unit 1802 obtains said actual skin input dose rate according to the result of said judgment unit 1801 and the relationship between the skin input dose rate at a reference position and the actual skin input dose rate.

Wherein, since the decision made by the judgment unit 1801 is that the angle Φ is less than 90 degrees, the second unit 18022 is then initiated, that is, computing the actual skin input dose rate with Equation (2):

$$R_S = \frac{D_1^2}{\left(D_2+D_3+\frac{D_5}{\cos\Phi}\right)^2} \times R_R \times e^{-K\frac{D_5}{\cos\Phi}(0 \oplus D_{AL})}$$

$$R_S = \frac{70^2}{\left(18+30+\frac{3}{\cos(30°)}\right)^2} \times 1 \times e^{-0.072 \times \frac{3}{\cos(30°)}(0 \oplus 0.7)} 1.74(\mu Gy/min)$$

Figure 5:
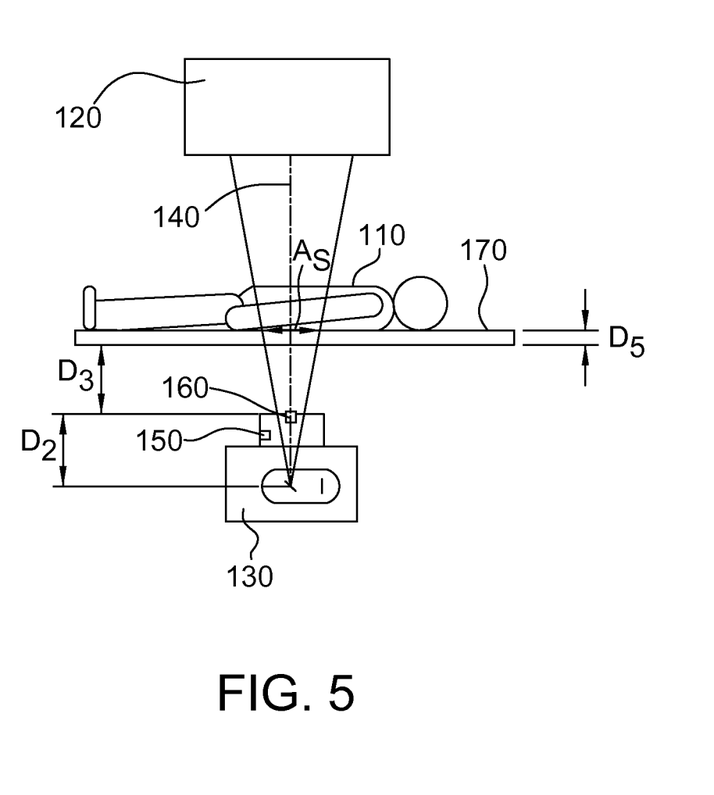
FIG. 5 is the diagram of an embodiment of the angle Φ sensed by an angle sensor being equal to 0 degree.

As in the case shown in FIG. 5, the distance $D_3$ sensed by the distance sensor 160 is 30 cm and the angle Φ sensed by the angle sensor 150 is 0 degree.

The judgment unit 1801 decides that this angle Φ (0 degree) is less than 90 degrees and the result unit 1802 obtains said actual skin input dose rate according to the result of said judgment unit 1801 and the relationship between the skin input dose rate at a reference position and the actual skin input dose rate.

Wherein, since the decision made by the judgment unit 1801 is that the angle Φ is less than 90 degrees, the second unit 18022 is then initiated, that is, computing the actual skin input dose rate with Equation (2):

$$R_S = \frac{D_1^2}{\left(D_2+D_3+\frac{D_5}{\cos\Phi}\right)^2} \times R_R \times e^{-K\frac{D_5}{\cos\Phi}(0 \oplus D_{AL})}$$

$$R_S = \frac{70^2}{\left(18+30+\frac{3}{\cos(0°)}\right)^2} \times 1 \times e^{-0.072 \times \frac{3}{\cos(0°)}(0 \oplus 0.7)} 1.52(\mu Gy/min)$$

Figure 2:
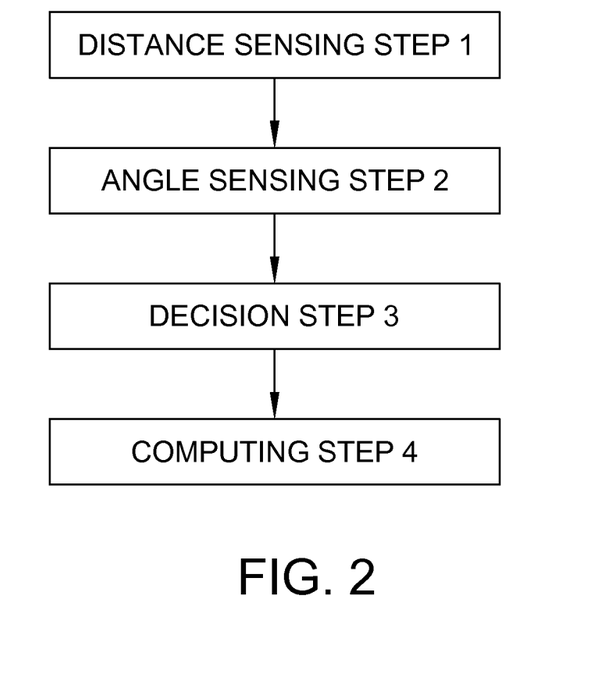
FIG. 2 is the flow chart of the actual skin input dose rate computing method in an X-ray machine according to the present invention.

The present invention also discloses a method for computing the actual skin input dose rate in an X-ray machine. As shown in FIG. 2 and FIG. 1, said X-ray machine comprises an X-ray source 130, an X-ray detector 120 disposed opposite to said X-ray source 130 and a supporting means 170 for supporting a subject 110.

The method includes an distance sensing step 1 including sensing a distance $D_3$ by a distance sensor 160 disposed in a direction directly opposite to said subject and close to the center of an X-ray beam but not within said X-ray beam.

The method also includes an angle sensing step 2 including sensing an angle Φ by an angle sensor 150 disposed at said X-ray source.

The method also includes a decision step 3 including deciding whether the angle Φ sensed by said angle sensor 150 is greater than or equal to 90 degrees or is less than 90 degrees.

The method also includes a computing step 4 including obtaining said actual skin input dose rate according to the result of said decision step and the relationship between the skin input dose rate at a reference position and the actual skin input dose rate.

If the result of said decision step is that the angle Φ is greater than or equal to 90 degrees, the actual skin input dose rate is computed using Equation (1):

$$R_S = \frac{D_1^2}{(D_2+D_3)^2} \times R_R \qquad \text{Eq. (1)}$$

wherein $D_1$ is a constant and indicates the distance between said X-ray source and the reference position, $D_2$ is a constant and indicates the distance between said X-ray source and said distance sensor 160, $D_3$ is the distance sensed by said distance sensor 160 and $R_R$ is the skin input dose rate at the reference position.

If the result of said decision step 3 is that the angle Φ is less than 90 degrees, the actual skin input dose rate is computed using Equation (2):

$$R_S = \frac{D_1^2}{\left(D_2+D_3+\frac{D_5}{\cos\Phi}\right)^2} \times R_R \times e^{-K\frac{D_5}{\cos\Phi}(0\oplus D_{AL})}$$

wherein $D_1$ is a constant and indicates the distance between said X-ray source and the reference position, $D_2$ is a constant and indicates the distance between said X-ray source and said distance sensor 160, $D_3$ is the distance sensed by said distance sensor 160, $R_R$ is the skin input dose rate at the reference position, $D_5$ is the thickness of said supporting means, K is the dose absorbing factor of AL given KV, and $D_{AL}$ is the equivalent aluminum attenuation value of said supporting means.

For an X-ray machine, $D_1$, $D_2$ and $D_5$ are constants, and in this example are assumed to be 70 cm, 18 cm and 3 cm respectively. In this example the equivalent aluminum attenuation of the supporting means 170 is $D_{AL}$=0.7 mm and the exposure condition is 70 k, then K=0.072, and according to U.S. Pat. No. 6,330,299 we can use Equation (8) to compute:

$$R_R = 1 \text{ μGy/min} \qquad \text{Eq. (8)}$$

For the case shown in FIG. 3, the actual skin input dose rate in this example is computed using the method for computing the actual skin input dose rate in an X-ray machine of the present invention.

First, the distance sensing step 1 is performed: sensing a distance $D_3$ by a distance sensor 160 disposed in a direction directly opposite to said subject and close to the center of an X-ray beam but not within said X-ray beam, which is 30 cm; then angle sensing step 2: sensing an angle Φ by an angle sensor 150 disposed at said X-ray source, which is 180 degrees; and then the decision step 3: deciding whether the angle Φ sensed by said angle sensor 150 is greater than or equal to 90 degrees or is less than 90 degrees, this step decides that the angle Φ (180 degrees) is greater than 90 degrees, thereby computing the actual skin input dose rate with Equation (1):

$$R_S = \frac{D_1^2}{(D_2+D_3)^2} \times R_R \qquad \text{Eq. (1)}$$

$$R_S = \frac{70^2}{(18+30)^2} \times 1 = 2.13 \text{ (μGy/min)}$$

For the case shown in FIG. 4, the actual skin input dose rate in this example is computed using the method for computing the actual skin input dose rate in an X-ray machine of the present invention.

First, the distance sensing step 1 is performed: sensing a distance $D_3$ by a distance sensor 160 disposed in a direction directly opposite to said subject and close to the center of an X-ray beam but not within said X-ray beam, which is 30 cm; then angle sensing step 2: sensing an angle Φ by an angle sensor 150 disposed at said X-ray source, which is 30 degrees; and then the decision step 3: deciding whether the angle Φ sensed by said angle sensor 150 is greater than or equal to 90 degrees or is less than 90 degrees, this step decides that the angle Φ (30 degrees) is less than 90 degrees, thereby computing the actual skin input dose rate with Equation (2):

$$R_S = \frac{D_1^2}{\left(D_2+D_3+\frac{D_5}{\cos\Phi}\right)^2} \times R_R \times e^{-K\frac{D_5}{\cos\Phi}(0\oplus D_{AL})} \qquad \text{Eq. (2)}$$

$$R_S = \frac{70^2}{\left(18+30+\frac{3}{\cos(30°)}\right)^2} \times$$

$$1 \times e^{-0.072 \times \frac{3}{\cos(30°)}(0\oplus 0.7)} 1.74 (\text{μGy/min})$$

For the case shown in FIG. 5, the actual skin input dose rate in this example is computed using the method for computing the actual skin input dose rate in an X-ray machine of the present invention.

First, the distance sensing step 1 is performed: sensing a distance $D_3$ by a distance sensor 160 disposed in a direction directly opposite to said subject and close to the center of X-ray beam but not within said X-ray beam, which is 30 cm; then angle sensing step 2: sensing an angle Φ by an angle sensor 150 disposed at said X-ray source, which is 0 degree; and then the decision step 3: deciding whether the angle Φ sensed by said angle sensor 150 is greater than or equal to 90 degrees or is less than 90 degrees, this step decides that the angle Φ (0 degree) is less than 90 degrees, thereby computing the actual skin input dose rate with Equation (2):

$$R_S = \frac{D_1^2}{\left(D_2+D_3+\frac{D_5}{\cos\Phi}\right)^2} \times R_R \times e^{-K\frac{D_5}{\cos\Phi}(0\oplus D_{AL})} \qquad \text{Eq. (2)}$$

$$R_S = \frac{70^2}{\left(18+30+\frac{3}{\cos(0°)}\right)^2} \times$$

$$1 \times e^{-0.072 \times \frac{3}{\cos(0°)}(0\oplus 0.7)} 1.52 (\text{μGy/min})$$

Moreover, the present invention discloses an X-ray machine, comprising an X-ray source, an X-ray detector disposed opposite to said X-ray source and a supporting means for supporting a subject. The X-ray machine further comprises an actual skin input dose rate computing device.

The actual skin input dose rate computing device includes a distance sensor 160 disposed in a direction directly opposite to said subject and close to the center of an X-ray beam but not within said X-ray beam and an angle sensor 150 disposed at said X-ray source as well as a computing unit 180. The computing unit 180 includes a judgment unit 1801 for deciding whether the angle Φ sensed by the angle sensor 150 is greater than or equal to 90 degrees or is less than 90 degrees, and a result unit 1802 for obtaining the actual skin input dose rate according to the result of the judgment unit 1801 and the relationship between the skin input dose rate at a reference position and the actual skin input dose rate.

Further, said result unit 1802 comprises a first unit 18021 and a second unit 18022, wherein if the angle Φ sensed by said angle sensor 150 is greater than or equal to 90 degrees, said first unit 18021 computes the actual skin input dose rate using Equation (1):

$$R_S = \frac{D_1^2}{(D_2 + D_3)^2} \times R_R \qquad \text{Eq. (1)}$$

wherein $D_1$ is a constant and indicates the distance between said X-ray source and the reference position, $D_2$ is a constant and indicates the distance between said X-ray source and said distance sensor 160, $D_3$ is the distance sensed by said distance sensor 160 and $R_R$ is the skin input dose rate at the reference position.

If the angle Φ sensed by said angle sensor 150 is less than 90 degrees, said second unit 18022 computes the actual skin input dose rate using Equation (2):

$$R_S = \frac{D_1^2}{\left(D_2 + D_3 + \frac{D_5}{\cos\Phi}\right)^2} \times R_R \times e^{-K\frac{D_5}{\cos\Phi}(0 \oplus D_{AL})} \qquad \text{Eq. (2)}$$

wherein $D_1$ is a constant and indicates the distance between said X-ray source and the reference position, $D_2$ is a constant and indicates the distance between said X-ray source and said distance sensor 160, $D_3$ is the distance sensed by said distance sensor, $R_R$ is the skin input dose rate at the reference position, $D_5$ is the thickness of said supporting means, K is the dose absorbing factor of AL, and $D_{AL}$ is the equivalent aluminum attenuation value of said supporting means.

In summary, the technical solution of the present invention could precisely obtain the actual skin input dose rate, which is very practical and effective such that the doctor could know the actual skin input dose rate upon the subject so that the subject could be protected effectively and the harm caused to the subject by X-ray could be minimized while an effective and correct diagnosis for the subject could be made.

Although the features of the present invention have been described by means of specific embodiments, various modifications and equivalent changes could be made to the present invention without departing from the spirit and scope of the present invention. All these modifications and equivalent changes are all intended to be comprised in the scope defined by the following claims.

What is claimed is:

1. An actual skin input dose rate computing device for use with an X-ray machine that includes an X-ray source, an X-ray detector disposed opposite to the X-ray source, and a supporting means for supporting a subject, said actual skin input dose rate computing device comprising:
   a distance sensor disposed in a direction directly opposite to the subject and close to an X-ray beam but not within the X-ray beam;
   an angle sensor disposed at the X-ray source; and
   a computing unit comprising:
      a judgment unit configured to determine whether an angle Φ sensed by said angle sensor is greater than or equal to 90 degrees or is less than 90 degrees; and
      a result unit configured to obtain actual skin input dose rate according to the result of said judgment unit and a relationship between a skin input dose rate at a reference position and the actual skin input dose rate, wherein said result unit comprises a first unit and a second unit, wherein if the angle Φ sensed by said angle sensor is greater than or equal to 90 degrees, said first unit computes the actual skin input dose rate using the following equation:

$$R_S = \frac{D_1^2}{(D_2 + D_3)^2} \times R_R$$

wherein $D_1$ is a constant and indicates a distance between the X-ray source and the reference position, $D_2$ is a constant and indicates a distance between the X-ray source and said distance sensor, $D_3$ is a distance sensed by said distance sensor and $R_R$ is the skin input dose rate at the reference position; and
   if the angle Φ sensed by said angle sensor is less than 90 degrees, said second unit computes the actual skin input dose rate using the following equation:

$$R_S = \frac{D_1^2}{\left(D_2 + D_3 + \frac{D_5}{\cos\Phi}\right)^2} \times R_R \times e^{-K\frac{D_5}{\cos\Phi}(0 \oplus D_{AL})}$$

wherein $D_1$ is a constant and indicates the distance between the X-ray source and the reference position, $D_2$ is a constant and indicates the distance between the X-ray source and said distance sensor, $D_3$ is the distance sensed by said distance sensor, $R_R$ is the skin input dose rate at the reference position, $D_5$ is a thickness of the supporting means, K is a dose absorbing factor of aluminum, and $D_{AL}$ is an equivalent aluminum attenuation value of the supporting means.

2. The actual skin input dose rate computing device of claim 1, wherein said angle sensor is configured to sense the angle Φ between a plumb line and the center of the X-ray beam.

3. The actual skin input dose rate computing device of claim 1, wherein said result unit is further configured to determine a ratio of an X-ray beam area at the reference position to an actual X-ray beam area at the subject skin.

4. The actual skin input dose rate computing device of claim 3, wherein said result unit is further configured to:
   determine a reference dose area product (DAP) rate based on the skin input dose rate at the reference position and the X-ray beam area at the reference position;
   determine an actual DAP rate based on the actual skin input dose rate at the subject skin and the X-ray beam area at the subject skin; and
   compare the reference DAP rate to the actual DAP rate.

5. The actual skin input dose rate computing device of claim 4, wherein said result unit is further configured to compute the actual skin input dose rate based on the ratio of the X-ray beam area at the reference position to the actual X-ray beam area at the subject skin, and the skin input dose rate at the reference position.

6. An actual skin input dose rate computing method in an X-ray machine that includes an X-ray source, an X-ray detector disposed opposite to the X-ray source, and a supporting means for supporting a subject, said computing method comprising:

sensing a distance by a distance sensor disposed in a direction directly opposite to the subject and close to an X-ray beam but not within the X-ray beam;

sensing an angle Φ by an angle sensor disposed at the X-ray source;

deciding whether the angle Φ sensed by the angle sensor is greater than or equal to 90 degrees or is less than 90 degrees; and obtaining an actual skin input dose rate according to a result of said decision step and a relationship between a skin input dose rate at a reference position and the actual skin input dose rate, wherein if the result of said decision step is that the angle Φ is greater than or equal to 90 degrees, computing the actual skin input dose rate using the following equation:

$$R_S = \frac{D_1^2}{(D_2+D_3)^2} \times R_R$$

wherein $D_1$ is a constant and indicates a distance between the X-ray source and the reference position, $D_2$ is a constant and indicates a distance between the X-ray source and the distance sensor, $D_3$ is the distance sensed by the distance sensor and $R_R$ is the skin input dose rate at the reference position, and wherein if the result of said decision step is that the angle Φ is less than 90 degrees, computing the actual skin input dose rate using the following equation:

$$R_S = \frac{D_1^2}{\left(D_2+D_3+\frac{D_5}{\cos\Phi}\right)^2} \times R_R \times e^{-K\frac{D_5}{\cos\Phi}(0 \oplus D_{AL})}$$

wherein $D_1$ is a constant and indicates the distance between the X-ray source and the reference position, $D_2$ is a constant and indicates the distance between the X-ray source and the distance sensor, $D_3$ is the distance sensed by the distance sensor, $R_R$ is the skin input dose rate at the reference position, $D_5$ is a thickness of the supporting means, K is a dose absorbing factor of aluminum, and $D_{AL}$ is an equivalent aluminum attenuation value of the supporting means.

7. The actual skin input dose rate computing method of claim 6, further comprising detecting the X-ray beam using the X-ray detector.

8. The actual skin input dose rate computing method of claim 6, wherein sensing a distance comprises sensing the angle Φ between a plumb line and the center of the X-ray beam.

9. The actual skin input dose rate computing method of claim 6, wherein obtaining an actual skin input dose rate comprises determining a ratio of an X-ray beam area at the reference position to an actual X-ray beam area at the subject skin.

10. The actual skin input dose rate computing method of claim 9, wherein obtaining an actual skin input dose rate further comprises:

determining a reference dose area product (DAP) rate based on the skin input dose rate at the reference position and the X-ray beam area at the reference position;

determining an actual DAP rate based on the actual skin input dose rate at the subject skin and the X-ray beam area at the subject skin; and comparing the reference DAP rate to the actual DAP rate.

11. The actual skin input dose rate computing method of claim 10, wherein obtaining an actual skin input dose rate comprises computing the actual skin input dose rate based on the ratio of the X-ray beam area at the reference position to the actual X-ray beam area at the subject skin, and the skin input dose rate at the reference position.

12. An X-ray machine comprising:

an X-ray source;

an X-ray detector disposed opposite to said X-ray source;

a supporting means for supporting a subject;

an actual skin input dose rate computing device comprising:

a distance sensor disposed in a direction directly opposite to the subject and close to an X-ray beam but not within the X-ray beam;

an angle sensor disposed at said X-ray source; and a computing unit comprising:

a judgment unit configured to determine whether an angle Φ sensed by said angle sensor is greater than or equal to 90 degrees or is less than 90 degrees; and a result unit configured to obtain actual skin input dose rate according to the result of said judgment unit and a relationship between a skin input dose rate at a reference position and the actual skin input dose rate, wherein said result unit comprises a first unit and a second unit, wherein if the angle Φ sensed by said angle sensor is greater than or equal to 90 degrees, said first unit computes the actual skin input dose rate using the following equation:

$$R_S = \frac{D_1^2}{(D_2+D_3)^2} \times R_R$$

wherein $D_1$ is a constant and indicates a distance between said X-ray source and the reference position, $D_2$ is a constant and indicates a distance between said X-ray source and said distance sensor, $D_3$ is a distance sensed by said distance sensor and $R_R$ is the skin input dose rate at the reference position;

and if the angle Φ sensed by said angle sensor is less than 90 degrees, said second unit computes the actual skin input dose rate using the following equation:

$$R_S = \frac{D_1^2}{\left(D_2+D_3+\frac{D_5}{\cos\Phi}\right)^2} \times R_R \times e^{-K\frac{D_5}{\cos\Phi}(0 \oplus D_{AL})}$$

wherein $D_1$ is a constant and indicates the distance between said X-ray source and the reference position, $D_2$ is a constant and indicates the distance between said X-ray source and said distance sensor, $D_3$ is the distance sensed by said distance sensor, $R_R$ is the skin input dose rate at the reference position, $D_5$ is a thickness of said supporting means, K is a dose absorbing factor of aluminum, and $D_{AL}$, is an equivalent aluminum attenuation value of said supporting means.

13. The X-ray machine of claim 12, wherein said X-ray detector comprises an image intensifier.

14. The X-ray machine of claim 12, wherein said angle sensor is configured to sense the angle $\Phi$ between a plumb line and the center of the X-ray beam.

15. The X-ray machine of claim 12, wherein said result unit is further configured to determine a ratio of an X-ray beam area at the reference position to an actual X-ray beam area at the subject skin.

16. The X-ray machine of claim 15, wherein said result unit is further configured to:
  determine a reference dose area product (DAP) rate based on the skin input dose rate at the reference position and the X-ray beam area at the reference position;
  determine an actual DAP rate based on the actual skin input dose rate at the subject skin and the X-ray beam area at the subject skin; and
  compare the reference DAP rate to the actual DAP rate.

17. The X-ray machine of claim 16, wherein said result unit is further configured to compute the actual skin input dose rate based on the ratio of the X-ray beam area at the reference position to the actual X-ray beam area at the subject skin, and the skin input dose rate at the reference position.

* * * * *